United States Patent [19]

Nicolaou et al.

[11] 4,308,396
[45] Dec. 29, 1981

[54] THROMBOXANE A₂ ANALOGUES

[75] Inventors: Kyriacos C. Nicolaou, Havertown, Pa.; Ronald L. Magolda, Vineland, N.J.

[73] Assignee: Research Corporation, New York, N.Y.

[21] Appl. No.: 19,932

[22] Filed: Mar. 12, 1979

[51] Int. Cl.³ .................... C07C 57/26; C07C 69/608; C07C 103/19
[52] U.S. Cl. .................................. 560/118; 562/500; 564/188; 424/505; 424/317; 424/320
[58] Field of Search ........................ 560/118; 562/500; 260/557; 564/188

[56] References Cited

PUBLICATIONS

Ansell et al., Fourth International Prostaglandins Conference Abstracts, May 27, 1979.

*Primary Examiner*—Robert Gerstl
*Attorney, Agent, or Firm*—Oblon, Fisher, Spivak, McClelland & Maier

[57] ABSTRACT

Stable biologically active thromboxane A₂ analogues having the formula

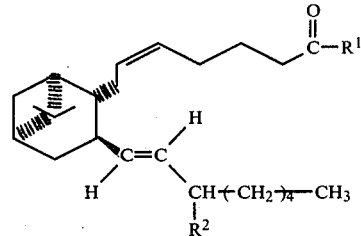

wherein
R¹ is OR³, where R³ represents hydrogen or a pharmaceutically acceptable cation or lower alkyl group; or
R¹ is NR⁴R⁵ where R⁴ and R⁵ are the same or different substituents selected from the group consisting of hydrogen and lower alkyl group; and
R² is hydrogen or an —OH group.

12 Claims, 4 Drawing Figures

THROMBOXANE A₂ ANALOGUES

This invention was made in the course of sponsorship by the National Institutes of Health and the support is hereby acknowledged. The invention described herein was made in the course of work under a grant or award from the Department of Health and Human Services.

BACKGROUND OF THE INVENTION

1. Field of the Invention

This invention relates to stable, biologically active analogues of thromboxane A₂ useful as antithrombotic agents.

2. Description of the Prior Art

The prostaglandins were first discovered in the 1920's and have proven since then to be among the most ubiquitous pharmaceutically active compounds ever tested. Their use and the use of analogues and derivatives thereof, has been suggested in as wide a range of applications as fertility control, induction of labor, regulation of blood pressure, regulation of blood clotting, control of asthma, anticonvulsion, antidepressing action and many others. A new compound has recently been discovered (Nature 263, 663 (1976); *Prostaglandins*, vol. 12, 685 and 715 (1976); Chem. and Engineering News, Dec. 20, 1976) which belongs to the general family of prostaglandins. The compound has been named prostacyclin and its structure has been proven by synthesis (Johnson, et al, *Prostaglandins*, 12, 915 (1976); Corey et al, J. Amer. Chem. Soc., 99, 2006 (1977) to be that of formula I. (The numbering system for prostacyclins is given for reference):

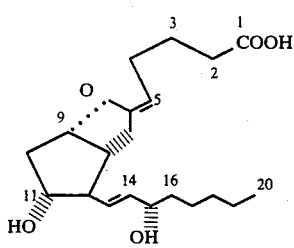
(I)

Its generic name is 6,9α-oxido-11α, 15α-dihydroxy-prosta (Z) 5, E(13)-dienoic acid. Prostacyclin is the most potent inhibitor of blood platelet aggregation of all the prostaglandins discovered to date. It has also been shown that prostacyclin destroys platelet aggregates after they have formed and that it has, in addition, a powerful action as a dilator of blood vessels. A second compound, which acts in an exactly opposite way to prostacyclin, has also recently been discovered by Hamberg and coworkers (Proc. Nat. Acad. of Sciences, U.S.A., 72, 2994 (1975)). This metabolite, named thromboxane A₂ (TA₂) and shown in formula II below has potent thrombotic and smooth muscle constricting properties:

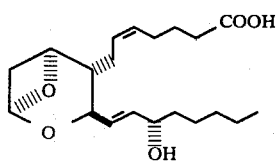
(II)

Both prostacyclin (I) and TA₂ (II) are derived from a common intermediate called endoperoxide, which in turn is synthesized from Arachidonic Acid by the enzyme cyclooxygenase. Prostacyclin is rapidly decomposed to 6-ketoprostaglandin $F_1\alpha$ (6-heto $PGF_1\alpha$) and TA₂ is rapidly decomposed to thromboxane B₂ (TB₂), less active final products in both cases. Both prostacyclin and TA₂ have very short half-lives under physiological conditions; that of prostacyclin being about 2 minutes and that of TA₂ only a mere 30 seconds at pH 7.4 and 37° C. The lability of TA₂ is caused by the presence of a sensitive bicyclic acetal system. The relationships between these metabolites, their precursors, products, and the enzymatic systems catalyzing their formation and decompositions, are summarized in Scheme I:

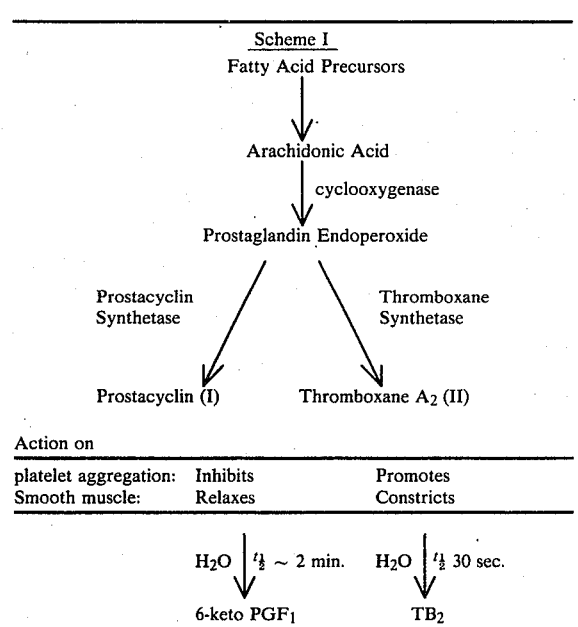

It can be seen that prostacyclin (produced by vascular endothelium) and thromboxane A₂ (produced by platelets) have opposite physiological effects and are very short lived. The balance between the levels of prostacyclin and thromboxane A₂, appears to maintain a finely tuned equilibrium between blood platelet aggregation versus dissolution and arterial constriction versus dilation.

Other important physiological effects which are mediated by the opposite transient actions of prostacyclin and TA₂ are the maintenance of the normal integrity of vessel walls, limitation of thrombus formation, assistance in the formation of hemostatic plugs by diminished prostacyclin formation, blood pressure regulation, control of inflammation, prevention of gastric ulceration and other similar effects. The pharmacological use of these metabolites however, is severely hindered by their short half-lives, especially so in the case of TA₂. Externally provided TA₂ will fail to reach its target tissues intact in high enough concentrations to cause any effects. Furthermore, the need to maintain the drug in a totally anhydrous condition also prevents its ready shipment, storage and testing for pharmacological applications. Therefore, if an analogue or derivative of TA₂ can be found which is stable and shows biological effects on blood platelets and arteries, such analogue would have wide applications in pharmacology and the treatment of cardiovascular and related diseases. The use of such a stable analogue of TA$_2$ can be used for patients with cardiovascular diseases, such as thrombosis, heart attack, or arteriosclerosis. It can be used in shock, such as hemorrhagic shock. Furthermore, if a stable analogue of TA$_2$ could be prepared and acted as an inhibitor of thromboxane synthetase it would be useful as an agent to control formation of TA$_2$ and serve as an antithrombotic agent.

However, although several stable bioactive prostacyclin analogues have been reported (see, e.g., Nicolaou et al, Angewandte Chemie, Int. Ed. (English) 17, 293 (1978) and references cited therein; also U.S. Patent Application Ser. No. 886,141, filed Mar. 13, 1978, there has been, prior to this invention, no report or preparation of a stable TA$_2$ analogue with biological activity.

SUMMARY OF THE INVENTION

It is therefore an object of this invention to provide an antithrombotic agent.

Another object of the invention is to provide an inhibitor of coronary artery constriction and of thromboxane synthetase.

Still another object of the invention is to provide a stable biologically active analogue of thromboxane A$_2$.

A further object of the invention is to provide a stable biologically active analogue of thromboxane A$_2$ wherein the labile cyclic acetal linkages have been replaced by carbon atoms.

Briefly, these and other objects of the invention which will hereinafter become more readily apparent, have been achieved by providing pharmaceutically active, stable analogues of thromboxane A$_2$ having the formula (III):

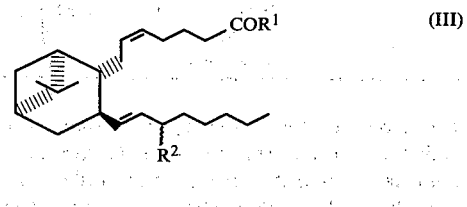

wherein
R$^1$ is OR$^3$ where R$^3$ represents hydrogen or a pharmaceutically acceptable cation or lower alkyl group; or
R$^1$ is NR$^4$R$^5$ where R$^4$ and R$^5$ are the same or different and are selected from the group consisting of hydrogen and lower alkyl group;
and wherein R$^2$ is hydrogen or —OH.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein.

DESCRIPTION OF THE PREFERRED EMBODIMENTS

Figure 1:
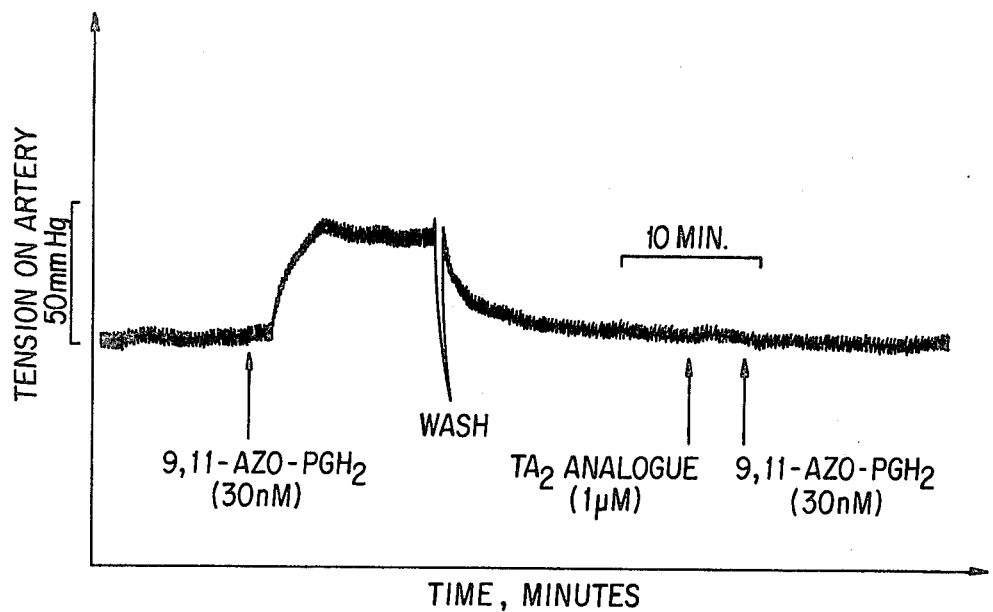
FIG. 1 is a graph showing the cat coronary arterial constriction caused by 9, 11-azo prostaglandin endoperoxide (9, 11-azo-PGH$_2$) a known constrictor, and antagonism of such constriction by a TA$_2$ analogue of the present invention.

The compounds of the present invention are stable pharmaceutically active thromboxane analogues of the formula (III), shown below with a numbering system based on the prostaglandin system:

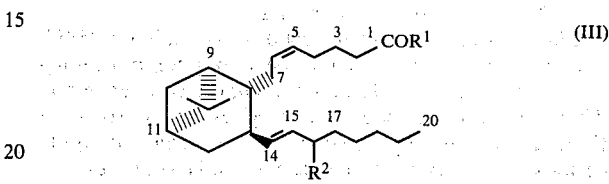

wherein
R$^1$ is either OR$^3$, where R$^3$ represents hydrogen or a pharmaceutically acceptable cation or lower alkyl group; or
R$^1$ is NR$^4$R$^5$ where R$^4$ and R$^5$ are the same or different and are selected from the group consisting of hydrogen and lower alkyl group; and wherein
R$^2$ is hydrogen or hydroxy group.

Pharmaceutically acceptable cations useful for the purposes of this invention are for example pharmaceutically acceptable metal cations or amine cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1, 3-propanediol, 2-amino-2-methyl-1-propanol, tris(hydroxymethyl) aminomethane, N-phenylethanolamine, N-(p-tert-amylphenyl)diethanolamine, galactamine, N-methyl-glucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Pharmaceutically acceptable lower alkyl groups are those derived from $C_1$-$C_{10}$ hydrocarbyl residues, especially $C_1$-$C_4$. Most preferred are methyl and ethyl groups.

When $R^2$=OH, two possible isomers at position 16 are possible (16R and 16S); the 16S isomer is preferred. The free acids ($R^1$=OH), their esters ($R^1$=Oalkyl), salts ($R^1$=O-cation) and amides ($R^1$=N(Alkyl)$_2$ or NH$_2$ or NH(alkyl)) of the thromboxane analogues are all encompassed by the present invention. Specific compounds of the present invention are for example:

Compound III wherein $R^1$=$R^2$=OH ($R^2$ is 16S),
Compound III, wherein $R^1$=OLi, ONa, OK or OCs and $R^2$=OH (16S);
wherein $R^1$=OCH$_3$ and $R^2$=OH (16S);
wherein $R^1$=N(CH$_3$)$_2$ and $R^2$=OH (16S);
wherein $R^1$=OH and $R^2$=H;
wherein $R^1$=OCH$_3$ and $R^2$=H;
wherein $R^1$=N(CH$_3$)$_2$ and $R^2$=H.

Gorman, R. et al, PNAS, U.S.A., 74, 4007 (1977) and Fitzpatrick, F. A., et al, Nature, 275, 764 (1978) have shown that prostaglandin endoperoxide (PGH$_2$) analogues which lack an —OH group at the 15 position are strong inhibitors of platelet aggregation. Thus for example 15-deoxy-9,11-azo-PGH$_2$-a compound which contains an azo functionality bridging positions 9,11-inhibits platelet aggregation while the 15 —OH analogue has aggregating activity. 15-deoxy-9,11-epoxyimino-PGH$_2$, another stable PGH$_2$ analogue also inhibits platelet aggregation. Therefore, the thromboxane analogues of the present invention include in one of their preferred embodiments, compounds wherein $R^2$=H, as shown above.

The $C_1$-amide derivatives of prostaglandin PGF$_2\alpha$ have been shown to be antagonistic to the action of the natural PGF$_2\alpha$ free acids by Ramwell, P. and his co-workers (Ramwell, P. et al, Nature, 278, 549 (1978)). The use of the C-1 amides in the present invention is thus also one of the preferred embodiments.

The compounds of the present invention can be prepared from (—)-myrtenol (IV) or its derivative by a series of condensation and alkylation reactions.

(—)-Myrtenol, an $\alpha,\beta$ unsaturated pinane alcohol derivative, is shown below, (IV, $R^6$=CH$_2$OH).

(IV)

It is first oxidized to the corresponding $\alpha, \beta$ unsaturated aldehyde (IV, $R^6$=—CHO) by a mild oxidation treatment, such as with MnO$_2$, Jones reagent or other similar oxidants such as CrO$_3$ complexes. The resulting aldehyde is then reacted in a Micheal-type 1,4 addition with an unsaturated anionic alkyl of the type shown in formula V.

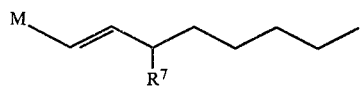
(V)

In formula V, $R^7$ represents hydrogen or a protected hydroxy group OR$^8$, where $R^8$ is any hydroxy group-protecting agent, such as an acyl group, a silyl group or a tetrahydropyranyl (THP) group. Preferred is a silyl group, such as tert-butyldimethylsilyl. M represents a cation or cation combination, such as lithium or copper/lithium, or M may be a Grignard-type cation/anion combination such as —MgBr. The reaction is carried out at a temperature of —78° C. to —50° C., in a solvent such as diethyl ether or tetrahydrofuran. The product of this reaction is an aldehyde of Formula VI ($R^6$=—CHO) wherein $R^7$ has the meaning described previously and wherein the stereochemistry of the

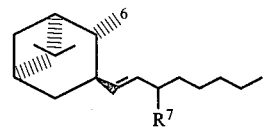
(VI)

substituent $R^6$ is predominantly trans to the substituent at position C-13. This stereochemistry is a result of the interaction between attacking reagent V and the $\alpha, \beta$ unsaturated aldehyde IV ($R^6$=—CHO), wherein the reagent V attacks the aldehyde from the less hindered face, i.e. away from the dimethyl bridge of the pinane skeleton. Aldehyde VI (R=—CHO) is then transformed to an enol ether VI (R=—CH=CH—OR$^9$, wherein $R^9$ is a lower alkyl or an aryl group) by reaction with an aryloxy or alkoxymethylene Wittig reagent such as VII:

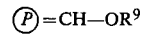=CH—OR$^9$ (VII)

wherein  represents a substituted or unsubstituted triarylphosphorane, such as triphenylphosphorane or tri-tolyl-phosphorane. Other aryloxy or alkoxymethylene Wittig reagents are for example those where Ⓟ represents a diarylphosphonate group $$\underset{(Ar_2\overset{\|}{P}-)}{\overset{O}{}}$$

where Ar is substituted or unsubstituted aryl, such as phenyl or tolyl. Preferred reagents are those where Ⓟ is triarylphosphorane, most preferably triphenylphosphorane, and where $R^9$ is methyl or ethyl, most preferably methyl. The reaction is carried out in a slight excess of the Wittig reagent (1.2-2.0 equivalents per equivalent of VI ($R^6$=CHO). Low temperatures and mixed organic or aqueous/organic solvents are useful. Aryloxy or alkoxy enol ether VI ($R^6$=—CH=CH—OR$^9$) is obtained as a mixture of 2 geometrical isomers (cis and trans). This enol ether is then hydrolyzed by standard methods to liberate the extended aldehyde VI ($R^6$=—CH$_2$—CHO). The hydrolysis may take place in acid and in the presence of absence of Lewis Acids such as metals which will assist hydration of the double bond. Both geometrical isomeric starting materials (cis- and trans-) are equally useful and may be used in the form of their mixture. Preferred reagents are Lewis acids such as Hg$^{+2}$ salts, most preferably Hg (OAc)$_2$ mixed with KI in an aqueous solvent, such as aqueous THF. Lewis acids such as Hg$^{+2}$ minimize side problems arising out of the deprotection of the protected hydroxy group at position C-16 ($R^7$=OR$^8$ (supra)). Such deprotection reactions should be minimized. The resulting extended aldehyde VI ($R^6$=—CH$_2$CHO) is then reacted with a Wittig reagent to complete the basic product skeleton III. The Wittig reagent is a carboxybutyl derivative represented by formula VIII:

$$\textcircled{P}=CH-CH_2-CH_2-CH_2-COOM \quad (VIII)$$

In this reagent, $\textcircled{P}$ represents a triarylphosphorane $(Ar_3P)$ or a diarylphosphonate group $(Ar_2P(O))$, as described above for the Wittig reagent VII. M represents an alkali metal salt, preferably sodium or potassium, or any other cationic component, such as ammonium or quaternary ammonium ion. The purpose of using a carboxylate salt rather than an ester is so as to minimize enolization of the hydrogen α to the carboxy group and therefore decrease side reactions. Any carboxy substituent which will achieve this, can be used successfully. The analogous Wittig reaction for prostaglandin derivatives has been used extensively and a description thereof may be found for example at J. S. Bindra and R. Bindra, "Prostaglandin Synthesis", Academic Press, New York, N.Y. 1977 and references therein, which is herein incorporated by reference. The just described Wittig condensation yields the carboxylate salt of inventive compound III ($R^1$=OM (see supra for definition of M), $R^2$=H or protected —OH group). Standard esterification methods will yield the corresponding esters III ($R^1$=$OR^3$, (supra)). Preferably diazoalkanes, such as diazomethane reactions are used. Amination of the esters with primary or secondary alkyl amines yields the corresponding amides III ($R^1$=$NR^4R^5$, supra)). When position C-16 is substituted by a protected hydroxy group, deprotection may be carried out by standard deprotection methodology, such as acidic treatment.

The compounds of this invention can be administered by any means that effects palliating conditions of cardiovascular complications in warm-blooded animals. For example, administration can be parenterally, subcutaneously, intravenously, intramuscularly or intraperitioneally. Alternatively or concurrently, administration can be by the oral route. The dosage administered will be dependent upon the age, health and weight of the recipient, kind of concurrent treatment if any, frequency of treatment, and the nature of the effect desired. Generally, daily dosage of active ingredient compounds will be from about 0.5 mg to 50 mg per kg of body weight. Normally, from 1 to 30 mg per kg per day, in one or more applications per day is effective to obtain the desired result. The compounds can be employed in dosage forms such as tablets, capsules, powder packets, or liquid solutions, suspensions, or elixirs, for oral administration, or sterile liquid for formulations such as solutions or suspensions for parenteral use. In such compositions, the active ingredient will ordinarily always be present in an amount of at least 0.5% by weight based on the total weight of the composition and not more than 90% by weight.

Table 1 describes the properties of one of the preferred compounds of formula III; i.e. $R^1$=$R^2$=OH, 16S:

TABLE 1

1. Inhibits Coronary Artery Contraction by Prostaglandin Endoperoxide Analogues, $ID_{50}$ 0.1 μM
2. Stabilizes Lysosomes at 1 μM
3. Inhibits Aggregation by Prostaglandin Endoperoxide Analogues, $ID_{50}$ 2.0 μM
4. Inhibits Thromboxane Synthetase, $ID_{50}$ 50 μM
5. Has no effect on Prostacyclin Synthetase at 100 μM
6. Has no effect on the Inhibition of Platelet Aggregation by Prostacyclin or Prostaglandin $D_2$ $ID_{50}$: Inhibitory dose which causes 50% inhibition of activity.

The thromboxane analogues of the present invention are useful in the treatment of thrombotic conditions, of blood clotting in heart attack cases, in artherosclerosis, diabetes and cerebral strokes. They are useful in the various types of shock, such as hemorrhagic shock.

Having generally described the invention, a more complete understanding can be obtained by reference to certain examples, which are included for purposes of illustration only and are not intended to be limiting unless otherwise specified.

I. Experimental Methods of Biological Testing

Thromboxane $A_2$ analogues (up to 4 μl of a 2.5 mM solution in ethanol) were tested for their effects on cat coronary arteries continuously prefused with 10 ml Krebs-Henseleit solution as described below.

Cats of either sex (2.5–3.5 kg) were anesthetized with sodium pentobarbital (30 mg/kg) given intravenously. Hearts were reapidly excised and placed in oxygenated (95% $O_2$+5% $CO_2$) ice-cold Krebs-Henseleit (K-H) solution of the following millimolar composition: NaCl, 118; KCl, 4.75; $CaCl_2.H_2O$, 2.54; $KH_2PO_4$, 1.19; $MgSO_4.7H_2O$, 1.19; $NaHCO_3$, 12.5; glucose, 10.00. A 20-gauge stainless steel cannula was inserted into the right coronary artery via the coronary ostium. Distal to the cannula, approximately 1 cm of coronary artery was dissected free of surrounding tissue. The section of right coronary artery with the cannula in place was excised from the heart and immediately transferred to a constant flow perfusion apparatus.

The perfusion apparatus consists of a reservoir containing 20 ml of warm (37° C.) oxygenated (95% $O_2$+5% $CO_2$) K-H solution which bathes the coronary artery and serves as recirculating perfusate. An increase in perfusion pressure indicates vasoconstriction, whereas a decrease in perfusion pressure signifies vasodilation. Following an initial 1 hr. equilibrium period, vascular responsiveness was established by adding 25 mM KCl. After washing with fresh K-H solution for 20–30 minutes, the preparation achieved a relatively constant low basal tone. Basal perfusion pressure averaged 50±2.5 mm Hg. Fresh K-H dilutions of stock thromboxane analog concentrations were added to the perfusate reservoir in 0.1–0.2 ml volumes. Changes in perfusion pressure in response to thromboxane analogue addition generally plateaus within 5 minutes of administration. Constriction of the arteries was induced by addition of 15 or 30 nM 9,11-azo-prostaglandinendoperoxide (azo-$PGH_2$), or 1 μM 9,11-methanoepoxy-$PGH_2$. These compounds and their effects are described in the following references: Corey et al, PNAS, U.S.A. 72, 3355 (1975); Bundy, G. L., Tetr.Lett, 1957 (1975); Malmsten, C., Life Sci, 18, 169 (1976) and Smith, J. B., et al, in *Platelets and Thrombosis,* Ed. by Mills, D.C.B. et al, Academic Press, London/N.Y. 1977, pp 83–95. The effect of thromboxane analogues on the release of cathepsin D from the cat liver large granule fraction was determined as described in Lefer, A. M. et al, Science 200, 52 (1978). The effect of thromboxane analogues on the release of cathepsin D from the cat liver large granule fraction was determined as described in Lefer, A. M. et al, Science 200, 52 (1978).

Platelet aggregation was studied in an aggregometer (Chronolog Corp., Phila., PA) using 0.5 ml citrated human platelet-rich plasma at 35° C. One minute after addition of analogue (up to 2 μl of a 25 mM solution in ethanol) aggregation was initiated by addition of sodium arachidonate (0.3–0.5 mM), ADP (2 μM) collagen (1 μg/ml), epinephrine (50 μM), 9,11-azo-$PGH_2$, (0.1–0.6 μM), 9,11-methanoepoxy-$PGH_2$, (0.3–0.6 μM), or 9,11-epoxy methano-PGH$_2$ (1–3 μM). The analogues were also tested for their effects on the inhibition of ADP-induced aggregation by 2 nM prostacyclin or 20 nM prostaglandin D$_2$.

To study the effects of analogues on thromboxane synthesis, rabbit platelets were washed free of plasma, resuspended in buffered saline solution and incubated at 37° C. for 5 minutes with analogues at either 10 μM or 100 μM. Radioactive 1-$^{14}$C-arachidonic acid (0.5 μCi, SA 50 Ci/mol, New England Nuclear, Boston, Mass.) was added and incubation was continued for 15 minutes, lipids were extracted by the method of Folch, J. Biol. Chem. 226, 497 (1957), and subjected to thin layer chromatography. In additional experiments, human platelet-rich plasma was incubated at 37° C. in the aggregometer for 1 minute with analogues. Sodium arachidonate (0.4 mM) was added and incubation was continued for 5 minutes. The samples were decanted into one-tenth vol. 100 mM EDTA, centrifuged for 2 minutes at 15,000 g, and thromboxane B$_2$ in the supernatant was determined by radioimmunoassay.

The effects of analogues on prostacyclin synthetase were determined using sheep vesicular glands as the enzyme source and 1-$^{14}$C-arachidonic acid as substrate essentially as described by Cottee, F. et al, in *Prostaglandins*, 14, 413 (1978).

II. Chemical Results

1. Synthesis of Pinane Thromboxane A$_2$, Methyl ester (III, R$^1$=OCH$_3$, R$^2$=OH (16S and 16R configurations)

(−) Myrtenol (IV, R$^6$=CH$_2$OH) was efficiently converted (95%) to the α,β, unsaturated aldehyde IV (R$^6$=—CHO) in the presence of MnO$_2$, in 48 hours at 25° C. in CH$_2$Cl$_2$ as solvent. The aldehyde IV (R$^6$=—CHO) underwent smooth 1,4-addition with the mixed cuprate derived from (±)-trans-lithio-1-octen-3-ol tert-butyldimethylsilyl ether and 1-pentynylcopper hexamethyltriamide complex (Corey, E. J., et al, *Tetrahedron Letters*, 737 (1976)), to afford aldehyde IXa:

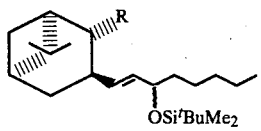

IXa, R = CHO
IXb, R = —CH=CH—OCH$_3$ (cis- and trans-)
IXc, R = —CH$_2$CHO

The 1,4-addition reaction was carried out in diethyl ether at −78° C., for 60 minutes and yielded 80% of IXa, which had $^{13}$C-NMR and $^1$H-NMR spectra consistent with trans-stereochemistry. Two epimers at C-16 were obtained.

Aldehyde IXa was condensed with 1.5 equivalents of methoxymethylenetriphenylphosphorane ((C$_6$H$_5$)$_3$P=CH—OCH$_3$) in toluene-THF solution at 0° C. to yield a mixture of the corresponding cis and trans enol ethers IXb in 94% yield from which aldehyde IXc was liberated with [Hg(OAc)$_2$—KI—H$_2$O—THF] quantitatively at 25° C. for 40 minutes. Aldehyde IXc was then reacted with the sodium salt of 4-carboxybutyltriphenylphosphorane in DMSO (1.5 equivalents), which led, after diazomethane treatment in ether to 80% yield of the methyl ester of protected thromboxane analogue Xa:

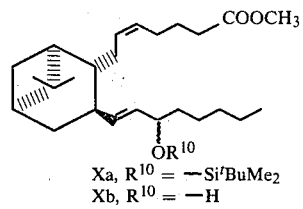

Xa, R$^{10}$ = —Si$^t$BuMe$_2$
Xb, R$^{10}$ = —H

Protected analogue Xa is a mixture of 2 epimers at C-16 (16R and 16S). Deprotection of the hydroxy group in acetic acid-H$_2$O—THF, 3:2:2 at 45° C. led to 100% of a 1:1 mixture of epimers Xb. These epimers were separated quantitatively by preparative thin layer chromatography (silica, ether-petroleum ether, 1:1; 16S isomer, R$_f$=0.53; 16R isomer, R$_f$=0.59). The 16S epimer of Xb showed the following properties: infrared spectrum, νmax 3400 (OH), 1742 cm$^{-1}$ (COOCH$_3$); $^1$H nuclear magnetic resonance spectrum (220 MHz, CDCl$_3$) τ4.40–4.78 (m, 4H, olefin), 5.95 (m, 1H, CH—O), 6.33 (s, 3H, COOCH$_3$), 8.80 and 8.94 (singlets, 3H each, pinane CH$_3$), 7.55–9.30 (m, 28H); $^{13}$C nuclear magnetic resonance spectrum (15 MHz, CDCl$_3$) ppm 174.02, 139.60, 131.16, 130.25, 138.95, 72.97, 51.41, 48.96, 41.74, 39.33, 38.62, 37.39, 34.92, 34.33, 33.55, 32.45, 31.74, 28.17, 26.67, 25.18, 24.92, 22.65, 14.01; mass spec m/e 390 (M$^+$); {α}$_D^{22}$+26.40° (methanol); Anal. Calcd for C$_{24}$H$_{40}$O$_3$: C 76.86; H 10.87, Found: C 77.05; H 11.08. The $^{13}$C NMR spectra of both epimers of Xb are of crucial value in assigning the stereochemistry of these compounds. In particular, the relatively low chemical shift of C-11 in the $^{13}$C NMR spectra of Xa (both epimers) (δ33.3=2) reveals the relative stereochemistry of the upper side chain by comparison to the corresponding model epimeric compounds from the myrtenol family, which exhibit this carbon at δ33.2 (C trans to the side chain) and 24.2 (C cis to the side chain) (Bohlmann, F, et al, *Organic Magnetic Resonance*, 1, 426 (1975)).

2. Preparations of Pinane Thromboxane A$_2$, free acid (III, R'=—OH, R$^2$=—OH)

Hydrolysis of the 16S epimer of Xb, prepared in example 1, with LiOH in aqueous THF at 25° C., furnished the corresponding free acid quantitatively, R$_f$=0.66, (silica, ether). Hydrolysis of the 16R epimer of Xb, as from Example 1, yielded 100% of the corresponding free acid, R$_f$=0.70 (silica, ether).

III. Biological Results

Coronary Artery Constriction

Incubation of cat coronary arteries with analogue III (R$^1$=—OH, R$^2$=16S, OH) (1 μm) abolished the constriction induced by 30 nM 9, 11-azo-PGH$_2$ (FIG. 1). Mean constrictions equivalent to 32 and 53 mm Hg were observed in three experiments at 15 nM and 30 nM 9,11-azo-PGH$_2$ respectively. At a concentration of 100 nM, the analogue reduced these constrictions by 73% and 50% respectively. Similar results were obtained in one experiment using 9,11-methanoepoxy-PGH$_2$ as the agonist.

At a final concentration of 1 μM, the analogue caused a significant inhibition (p<0.005) of the release of cathepsin D from cat liver lysosomes (4 experiments).

Platelet Aggregation

Figure 4:
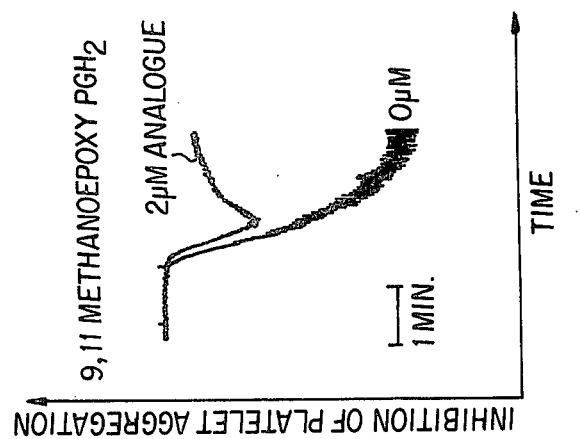
FIG. 4 shows the same effects as described in FIG. 2, except aggregation is caused by 1.43 μM 9,11-epoxymethano-PGH$_2$, a known aggregating agent.
Figure 3:
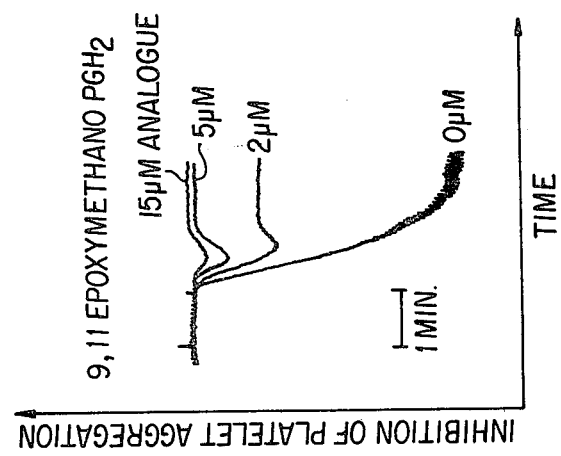
FIG. 3 shows the same effects as described in FIG. 2, except aggregation is caused by 0.29 μM 9,11-methanoepoxy-PGH$_2$, a known aggregating agent.
Figure 2:
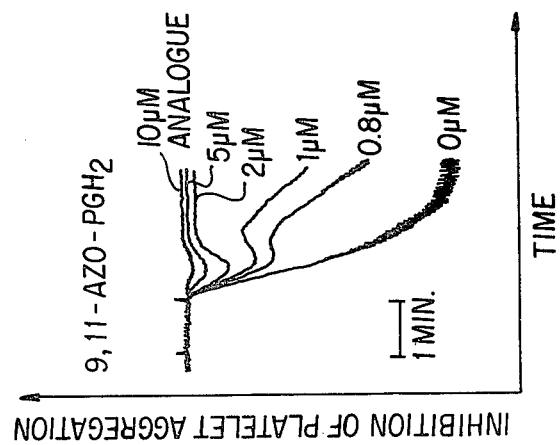
FIG. 2 shows the inhibitory effects of an analogue of TA$_2$ of the present invention on the aggregation of blood platelets, when the aggregation is caused by 0.18 μM 9,11-azo-PGH$_2$, a known aggregating agent.

The same analogue as above in intermediate concentrations (1–15 μM), inhibited the aggregation of human platelets induced by 9,11-azo-PGH$_2$, 9,11-epoxymethano-PGH$_2$ or 9,11-methanoepoxy-PGH$_2$ in a dose-dependent fashion (FIGS. 2, 3 and 4). Analogue at 10

μM abolished platelet aggregation induced by arachidonic acid, abolished the second wave of aggregation induced by ADP or epinephrine, and partially inhibited platelet aggregation induced by collagen. At this concentration, the analogue III ($R^1=R^2=OH$, 16S epimer) did not inhibit primary aggregation induced by ADP or epinephrine nor did it affect the inhibition of aggregation by prostacyclin or prostaglandin $D_2$. The 16R epimer of the analogue III ($R^1=R^2=-OH$) was approximately ten times less effective as a prostaglandin endoperoxide antagonist.

Thromboxane Synthetase

At 10 μM, the 16S analogue III ($R^1=R^2=OH$) inhibited the formation of thromboxane $B_2$ from 1-$^{14}$C-arachidonic acid by washed rabbit platelets by 23%. At 100 μM, 83% inhibition of thromboxane $B_2$ formation was observed. This was associated with corresponding increases in radioactive prostaglandins $E_2$, $D_2$ and $F_{2\alpha}$ indicating that the effect of the analogue was on thromboxane synthetase and not on cyclooxygenase. While the analogue, at 50 μM, abolished arachidonic acid-induced aggregation in human platelet-rich plasma, thromboxane $B_2$ formation was reduced by only 50%.

Having now fully described this invention, it will be apparent to one of ordinary skill in the art that many changes and modifications can be made thereto without changing the scope or meaning thereof.

What is claimed as new and intended to be covered by Letters Patent is:

1. Stable biologically active thromboxane $A_2$ analogues having the formula

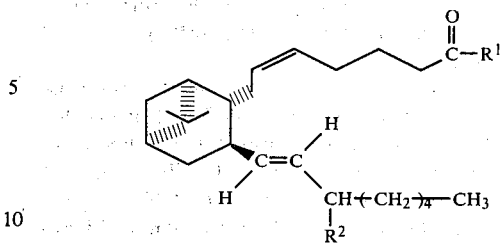

wherein
   $R^1$ is $OR^3$, where $R^3$ represents hydrogen or a pharmaceutically acceptable cation or lower alkyl group; or
   $R^1$ is $NR^4R^5$ where $R^4$ and $R^5$ are the same or different substituents selected from the group consisting of hydrogen and lower alkyl group; and
   $R^2$ is hydrogen or an —OH group.

2. The analogue of claim 1 wherein $R^1$ is $OR^3$ where $R^3$ represents a pharmaceutically acceptable cation, lower alkyl group, or hydrogen.

3. The analogue of claim 2, wherein $R^3$ represents a $C_1$-$C_4$ alkyl group.

4. The analogue of claim 2 wherein $R^3$ represents hydrogen.

5. The analogue of claim 2 wherein $R^3$ represents an alkali metal cation.

6. The analogue of claim 1 wherein $R^1$ is $NR^4R^5$ where $R^4$ and $R^5$ are the same or different substituents selected from the group consisting of hydrogen and lower alkyl groups.

7. The analogue of claim 6 wherein $R^4=R^5=$—$C_1$-$C_4$ alkyl groups.

8. The analogue of claim 7 wherein $R^4=R^5=$—$CH_3$.

9. The analogue of claim 1 wherein $R^2=H$.

10. The analogue of claim 1 wherein $R^2=$—OH.

11. The analogue of claim 1 wherein $R^1=$—$OCH_3$ and $R^2=$—OH, and wherein the absolute configuration around said $R^2$ substituent is S.

12. The analogue of claim 1 wherein $R^1=$—OH and $R^2=$—OH and wherein the absolute configuration around said $R^2$ substituent is S.

* * * * *